United States Patent
Taheri et al.

(10) Patent No.: US 9,340,470 B2
(45) Date of Patent: May 17, 2016

(54) PROCESS AND REACTOR FOR DEHYDRATION OF BUTANOL TO BUTYLENES

(71) Applicant: PETRON SCIENTECH INC., Princeton, NJ (US)

(72) Inventors: Hassan Taheri, Hinsdale, IL (US); Yogendra Sarin, Plainsboro, NJ (US); Brian Ozero, Westhampton Beach, NY (US)

(73) Assignee: Petron Scientech Inc, Princeton, NJ (US)

( * ) Notice: Subject to any disclaimer, the term of this patent is extended or adjusted under 35 U.S.C. 154(b) by 642 days.

(21) Appl. No.: 13/727,024

(22) Filed: Dec. 26, 2012

(65) Prior Publication Data

US 2014/0179965 A1    Jun. 26, 2014

(51) Int. Cl.
| | |
|---|---|
| *B01J 8/00* | (2006.01) |
| *B01J 8/02* | (2006.01) |
| *B01J 8/04* | (2006.01) |
| *C07C 1/24* | (2006.01) |
| *C07C 1/20* | (2006.01) |

(52) U.S. Cl.
CPC ............... *C07C 1/24* (2013.01); *C07C 2521/04* (2013.01)

(58) Field of Classification Search
CPC ........ C07C 1/20; C07C 1/24; C07C 2521/02; C07C 2521/04; B01J 8/00; B01J 8/02; B01J 8/04; B01J 8/0446; B01J 8/0449; B01J 8/0457
See application file for complete search history.

(56) References Cited

U.S. PATENT DOCUMENTS

| | | | | |
|---|---|---|---|---|
| 2,353,509 | A * | 7/1944 | Schulze ................. | B01J 8/0453 208/130 |
| 4,396,789 | A * | 8/1983 | Barrocas ................... | C07C 1/24 585/639 |
| 4,529,827 | A * | 7/1985 | Drake ...................... | B01J 21/04 502/355 |
| 2015/0265992 | A1* | 9/2015 | Taheri ........................ | B01J 8/06 422/632 |

* cited by examiner

*Primary Examiner* — Natasha Young
(74) *Attorney, Agent, or Firm* — Richard L. Moseley; Kenneth H. Johnson

(57) ABSTRACT

A reactor design and configuration and a process for the catalytic dehydration of butanol to butylenes where the reactor train is comprised of a multi-stage single reactor vessel or multiple reactor vessels wherein each stage and/or vessel has different length, internal diameter, and volume than the other stages and/or vessels and in addition the stages and/or reactor vessels are connected in series or in parallel arrangement, preferably used with an improved means of introducing the butanol feedstock and a heat carrying inert gas to the improved reactor train.

6 Claims, 2 Drawing Sheets

PROCESS AND REACTOR FOR DEHYDRATION OF BUTANOL TO BUTYLENES

BACKGROUND OF THE INVENTION

1. Field of the Invention

This invention relates to a process for the selective catalytic dehydration of n-butanol or iso-butanol (collectively referred to as butanol in this application) to mixed butylenes including 1-butylene, iso-butylene, and cis- and trans-2-butelens (herein collectively referred to as butylenes) using an improved technology of reactor design and configuration wherein the reactor train is comprised of a multi-stage single reactor vessel or multiple reactor vessels wherein each stage and/or vessel has different length, internal diameter, and volume than the other stages and/or vessels and in addition the stages and/or reactor vessels are connected in series or in parallel arrangement. Furthermore, this invention discloses an improved means of introducing the butanol feedstock and a heat carrying inert gas to the improved reactor train.

2. Related Information

The butylene isomers are important olefins which are extensively used commercially in the petrochemicals, chemicals, and oil industries. For example, isobutylene is the primary feedstock in the manufacture of viscous polybutenes which are extensively used in such diverse products as lubricating oils, anti-oxidants, additives, and other consumer goods. It is also a preferred raw material for alkylation process in the refining industry. Butylenes are also used in the production of synthetic rubber. Butylenes are primarily produced as secondary products from petroleum resources by the high temperature steam cracking of petroleum-derived feedstocks such as heavy naphtha, ethane/propane, or gas condensates. The economics of these processes are greatly influenced by the supply, availability, and price of crude oil and natural gas. In addition, the cracking processes produce large quantities of primary and valuable petrochemicals such as ethylene and propylene and other olefinic hydrocarbons. which have to be recovered and purified and therefore may not be ignored and disposed of as waste. The economics of the butylenes production by the steam cracking process thus require that these products be separated and recovered at very high purity suitable for downstream chemicals and polymer applications. This would require very complex processing scheme, high capital investment, and large energy consumption to separate, purify, and provide storage for all the primary and secondary products so that the steam cracking process can be economically justified. In addition, the success of the petroleum-derived butylenes requires that all the by-products be marketed to their respective end users. If a user of butylenes were interested in only producing butylenes and no other products, the cracking route is not a viable and profitable option. Furthermore, the conventional steam cracking produces large quantities of $CO_2$ (carbon) which is a main component of the greenhouse gas emission. The mixed butylenes formed by the process claimed herein can be easily isomerized to the desired butylene isomer by any one of several processes in commercial operation.

The dehydration of butanol is a simple and attractive potential route to butylenes. Presently, there is no known commercial process for the catalytic dehydration of butanol. Recently, as the biofuels have attracted more attention globally, as prices of crude oil have increased and have become more unpredictable, and as petroleum supply sources have become more unstable and problematic, the butanol dehydration process is gaining interest as an alternative source for the production of chemical- or polymer-grade butylenes. In addition, with the threat to the environment and limited resources in some parts of the world, the butanol dehydration process is being increasingly competitive with the traditional steam cracking process. Furthermore, the sources of raw materials for butanol supply are expanding with a resultant decrease in the cost of butanol manufacture thus making it an attractive option for butylenes production.

The butanol dehydration reaction basically is characterized by the removal of a water molecule from butanol and as such is highly endothermic. A significant amount of heat (energy) is thus required to initiate and sustain the reactions to completion. Therefore, the choice of the reactor, its design, and configuration are critical aspects of managing the thermal events within the reactor and controlling the operating temperatures within the catalyst bed for an economical process.

Additionally, the economic production of butylenes by this process largely depends on the high conversion of butanol feedstock to avoid recovery and recycle of any unreacted butanol. It also requires high selectivity and yield of the butylenes product in order to avoid expensive separation and purification of the final product which is needed for chemicals and polymer applications. Furthermore, it is critical to limit the formation of by-products which will complicate the recovery and purification of the primary product and its downstream applications into high value-added chemicals and polymers.

Unlike the ethanol dehydration process to ethylene which has been the subject of many patents and developments and which has been commercially practiced for many years, there have been no known patents and/or technical articles on the dehydration process of butanol to butylenes.

While the chemistry of the dehydration of alcohols to olefins is well understood, the successful development of a process for selective dehydration of butanol to butylenes requires that a reactor design be developed consistent with the thermodynamics and kinetics of the dehydration reactions. Foremost, the reactions in this process are highly endothermic which require input of considerable amount of energy to derive the process. Therefore, the supply of heat, the management of the thermal processes, and the reactor temperature control constitute important considerations for optimum performance. One aspect of the present invention is a reactor disclosure to address these issues.

With regard to alcohol dehydration reactors which have been proposed and developed in the past, several patents stand out. U.S. Pat. No. 4,134,926 discloses a fluidized bed reactor concept for the dehydration of ethanol to ethylene wherein a portion of the dehydration catalyst is continuously withdrawn from the reactor chamber and regenerated with air in a second fluid-bed regenerator. The hot regenerated catalyst is then mixed with fresh make-up catalyst and recycled back to the primary reactor to provide the endodermic heat of reaction. This reactor concept has not found commercial application due to the complexity of the process, the handling and recycle of large quantities of solid catalyst, and continuous replacement of the lost catalyst because of attrition.

U.S. Pat. No. 4,232,179 describes a reactor train invention in which multiple, adiabatic reactor vessels are connected in series and/or parallel arrangement for dehydration of ethanol to ethylene. This patent further teaches the use of a sensible heat carrying fluid such as steam mixed with the alcohol feedstock prior to feeding to individual reactors. Each reactor is packed with a solid catalyst. The energy required for the reactions is supplied by a fired heater wherein both alcohol feedstock and steam are heated to very high temperatures needed for the reactions to proceed to completion in each reactor stage. This feature, being similar to British patent 516,360, can also result in lower selectivity and yield of the primary product and the formation of problematic by-products. In addition, no distinction is made in this disclosure as to the relative sizes of each reactor and the catalyst bed within that reactor with respect to other reactors and/or catalyst beds which make up the reactor train.

U.S. Pat. No. 4,396,789 teaches an invention which is basically similar to U.S. Pat. No. 4,232,179 with the exception that the reactor train is designed to operate at a design pressure of between 20 and 40 atmospheres. The patent claims that such high pressure operation will simplify the purification of the crude olefin product during the subsequent cryogenic distillation to produce high quality olefin for downstream chemicals/polymer applications.

In all the above processes, the dehydration catalyst is subjected to carbonization and rapid fouling as a result of direct exposure of the alcohol to the very high coil surface temperatures within the fired pre-heater. This practice would therefore entail less than optimum performance of the catalyst and would require frequent regeneration of the catalyst bed thus requiring downtime, loss of production, and shortened catalyst life.

It is the general object of this invention to maximize the utilization efficiency of the dehydration of butanol feedstock to butylenes product while minimizing the production of undesirable by-products. The specific goal of the present invention is to provide a novel, adiabatic reactor design and configuration to achieve the desired goals of the invention. Additionally, another goal of the present invention is to disclose an efficient process for carrying out the dehydration reaction. Furthermore, it is an object of the present invention to utilize the available streams normally found within a production facility or derived from the operation of the dehydration process carried out in the reactor. Other objects and benefits of the present invention will become apparent to those experienced in the art in the following sections.

SUMMARY OF THE INVENTION

The present invention is an adiabatic gas phase process for catalytic dehydration of butanol to butylenes process comprising:
a) feeding butanol through several dehydration stages,
b) the stages are stacked in a series or parallel configuration,
c) each stage has a different internal diameter, length, and volume than the other stages,
d) each stage contains a quantity of fixed bed catalyst whose amount is different than the quantity in other stages within the reactor vessel, and
e) each stage is substantially circular.

A significant aspect of the present invention is an adiabatic gas phase reactor comprising:
a) a plurality of stages, preferably having a substantially circular dimension, such as a cylinder
b) each of said stages having an independently determined internal diameter, length, and volume, and
c) each of said stages contains a quantity of fixed bed catalyst and inert support beds whose amount is independently determined, preferably wherein the independent determinations take into account the control of thermal energy, the optimization of temperature profiles within the catalyst beds, and the feed rates of butanol and inert gas to the individual stages of the reactor or external to the reactor to obtain the highest efficiency for butanol conversion, butylenes selectivity, and yield. The stages can be arranged in series or parallel or in combinations thereof.

The stages, whether housed in a single structure or in separate structures, comprise a reactor train where the dehydration reaction or process is carried out. Each structure is designed to operate under different conditions of temperature, pressure, reactant residence time, and quantity of catalyst than the other structures.

DETAILED DESCRIPTION OF THE INVENTION

Recognizing (i) the short comings of the prior art as noted above, (ii) the key economic drivers needed for bio-butylenes production to compete as replacement for petroleum-derived butylenes, and (iii) the specific quality demands required of any bio-butylenes as feedstock for the downstream chemicals and polymer applications, this invention provides an improved reactor technology and process to specifically address these issues. This disclosure teaches a novel reactor design and geometry and an improved processing concept to achieve its desired goals. The novel reactor is configured according to two embodiments. In each embodiment, the multiple reactor vessels and/or reactor stages are employed in series or in parallel configuration wherein each stage and/or reactor vessel comprising the reactor train has a different internal diameter, length, volume, and quantity of fixed-bed catalyst than the other stages and/or vessels. Several improvements arise from this novel design whose detail is illustrated below. The number of stages is typically between 2 and 10 and preferably between 2 and 5. Each stage preferably has an internal diameter of between 0.5 to 10 meters at the inlet to the stage and an internal diameter of between 0.7 and 15 meters at the outlet of the stage with each stage preferably having a length of between 0.3 to 15 meters.

Figure 1:
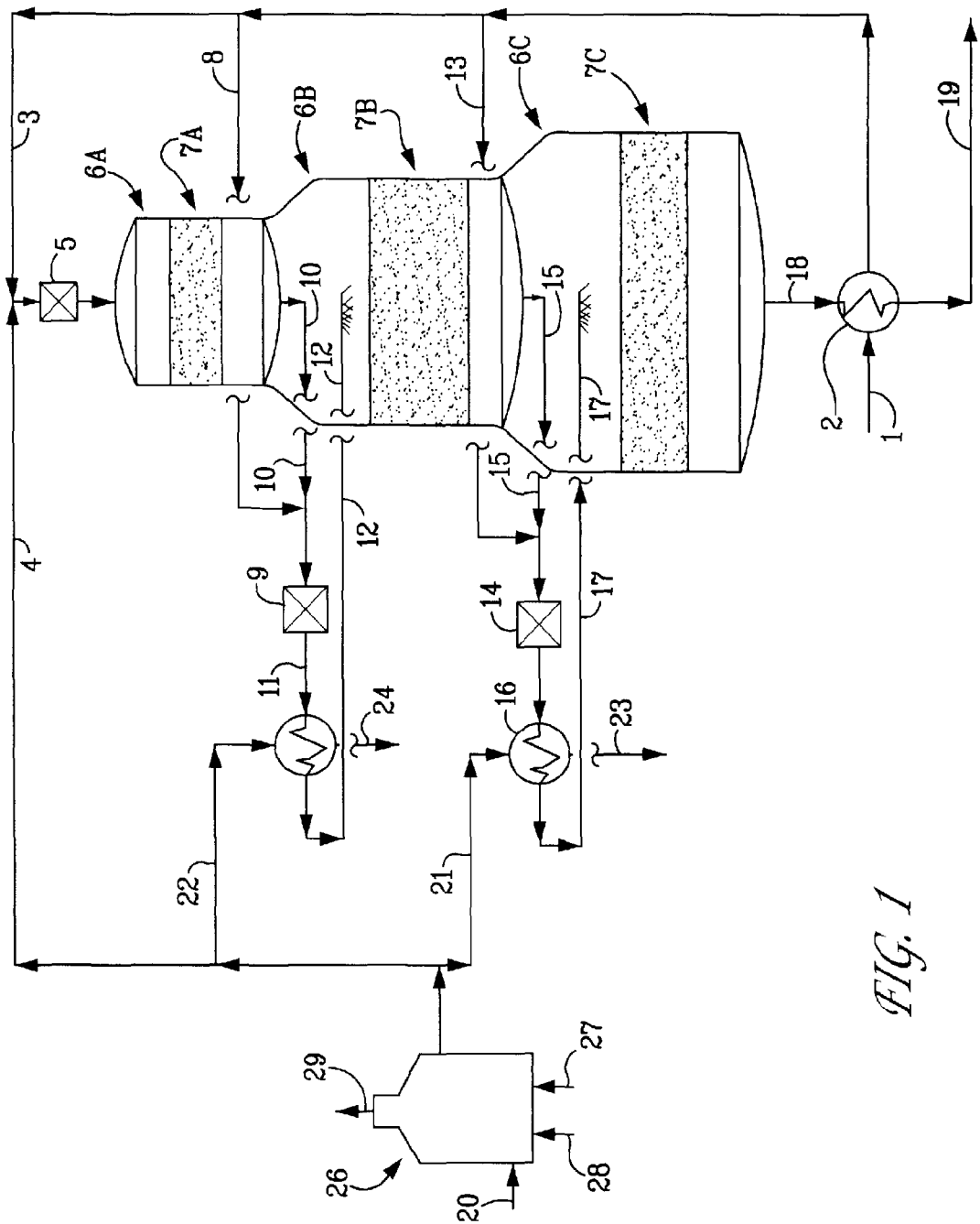
FIG. 1 shows a single reactor vessel housing three catalyst zones in series with each zone having different length, diameter, volume, and/or catalyst quantity than the other zones and the flow arrangement of the reactant alcohol and the inert gas.

According to this disclosure, two embodiments of this process will be described in the following sections. FIG. 1 serves to illustrate one embodiment of this invention. In this particular embodiment, one reactor vessel containing three stages which are connected in series is employed. The three stages comprise the reactor vessel. Each stage is packed with a suitable fixed-bed alcohol dehydration catalyst such as those described in U.S. Pat. Nos. 4,260,845, 4,302,357, 4,529,827, 4,670,620, 4,873,392, and 6,489,515, etc. and US application 2010/0249476. Each stage in this arrangement has a different internal diameter, length, volume, and quantity of catalyst than the other stages. The variable sized stages are uniquely designed for a target production of butylenes. The benefits and the improvements made possible by this design will become obvious after the detailed explanation of the invention.

Hydrous or anhydrous butanol stream 1 is first vaporized and preheated in heat exchanger 2 using the hot reactor effluent gases 18 which then exit as stream 19 to downstream purification sections of the plant (not shown). The butanol feed is not passed through a superheating furnace, but is separately pre-heated, to a temperature between 200° to 400° C. and mixed with the heat supplying inert gas in an in-line mixer 5 prior to being introduced into any stage. Butanol is added to each stage at a rate of between 0.01 to 10 kg per hour per kg catalyst and has a weight ratio of between 0.005 to 0.06 and preferably between 0.01 to 0.1 to the weight of the inert gas at the inlet to each stage. Within each stage as optimized according to the present invention, the operating temperature is from 200° C. to 550° C. and preferably from 300° C. to 500° C. at the inlet to each stage and wherein the outlet temperature of each stage is maintained at 200° C. to 500° C. and preferably from 250° C. to 450° C. at operating pressure of each stage is from 2 barg to 50 barg and preferably from 4 barg to 40 barg.

The feed butanol stream 1, after being heated in the exchanger 2, is divided into three streams 3, 8, and 13. Stream 3 is combined with superheated inert gas stream 4 which is supplied by the inert super-heater 26 wherein cold inert gas enters via stream 20 and the heat source is provided by burning fuel supplied by stream 27 and air supplied by stream 28. Alternatively, the superheated inert gas can be supplied via other plant facilities such as a cogeneration plant (not shown). The combustion products from the super-heater 26 leave the stack via stream 29. The inline stationary mixer 5 serves to fully mix the pre-heated butanol stream 3 and superheated stream 4 before entering the first stage reactor 6A. Stage 6A houses the fixed-bed bed catalyst 7A. The diameter, length, and the volume of catalyst in this stage is designed for optimum temperature profile and residence time distribution of the butanol reactant. Typically, the inlet temperature to this stage is between 250 to 550° C. and the outlet in the range of 200 to 480° C. The weight hourly space velocity (WHSV) of butanol in this stage is preferably in the range of 0.001 to 10 kg butanol per hour per kg of catalyst. Typically, the weight ratio of the inert gas to butanol in the inlet to this stage is between 0.1 to 10 kg butanol to one kg of inert gas. The operating pressure in this stage may range from 1 (preferably 2) to 50 barg. These conditions are designed to optimize the temperature profile in this stage and to achieve the complete conversion of butanol and greater than 99% selectivity to mixed butylenes.

The exit stream 10 from stage 6A containing butylenes from stage 1 and water formed in stage 1 is mixed outside of the reactor vessel with fresh butanol stream 8 in inline mixer 9 and heated to the desired temperature by exchanger 11. This exchanger is heated by superheated inert gas stream 22. The heat supplying inert gas to each reactor stage may be superheated steam at pressure in the range of 1 to 50 barg and preferably 4 to 40 barg and at temperature in the range of 300° C. to 550° C. and preferably 350° to 500° C. The inert gas exit from heat exchanger 11 as stream 24 and is used for other heat requirement in the plant. Stream 12 from exchanger 11 is fed to second stage reactor 6B and is distributed downward to the catalyst bed 7B in this stage. The ranges of conditions in this second stage include: inlet temperature of 2500-500° C., outlet temperature of 200-420° C., butanol WHSV of 0.01 to 8 kg butanol/hr/kg catalyst, butanol-to-inert gas ratio of 0.8 to 15 kg butanol/kg inert gas and pressure 1 to 50 barg. Again, the conditions are chosen such that to obtain optimum temperature profile through this second stage catalyst bed, to achieve complete conversion of butanol, and to realize >99% selectivity to butylenes.

The effluent stream 15 from second stage reactor is mixed with additional fresh butanol stream 13 in inline mixer 14, heated in exchanger 16. Exchanger 16 is heated by superheated inert gas 21. The heated stream 17 from exchanger 16 is the feed to a third reactor stage 6C which contains the 3$^{rd}$ stage catalyst bed 7C. The operating conditions in this stage are also optimized to achieve similar goals of temperature profile and performance as in stages 6A and 6B. The ranges of conditions in this third stage include: inlet temperature of 250-460° C., outlet temperature of 200-400° C., butanol WHSV of 0.01 to 6 kg butanol/hr/kg catalyst, butanol-to-inert gas ratio of 1 to 20 kg butanol/kg inert gas, and pressure in the range 1 to 50 barg. The exit stream 18 from stage 6C flows to heat exchanger 18. Stream 19 containing crude butylenes product, inert gas, the water formed in alcohol dehydration, and minor by-products exits this exchanger and is processed in downstream equipment for separation and purification or butylenes.

Figure 2:
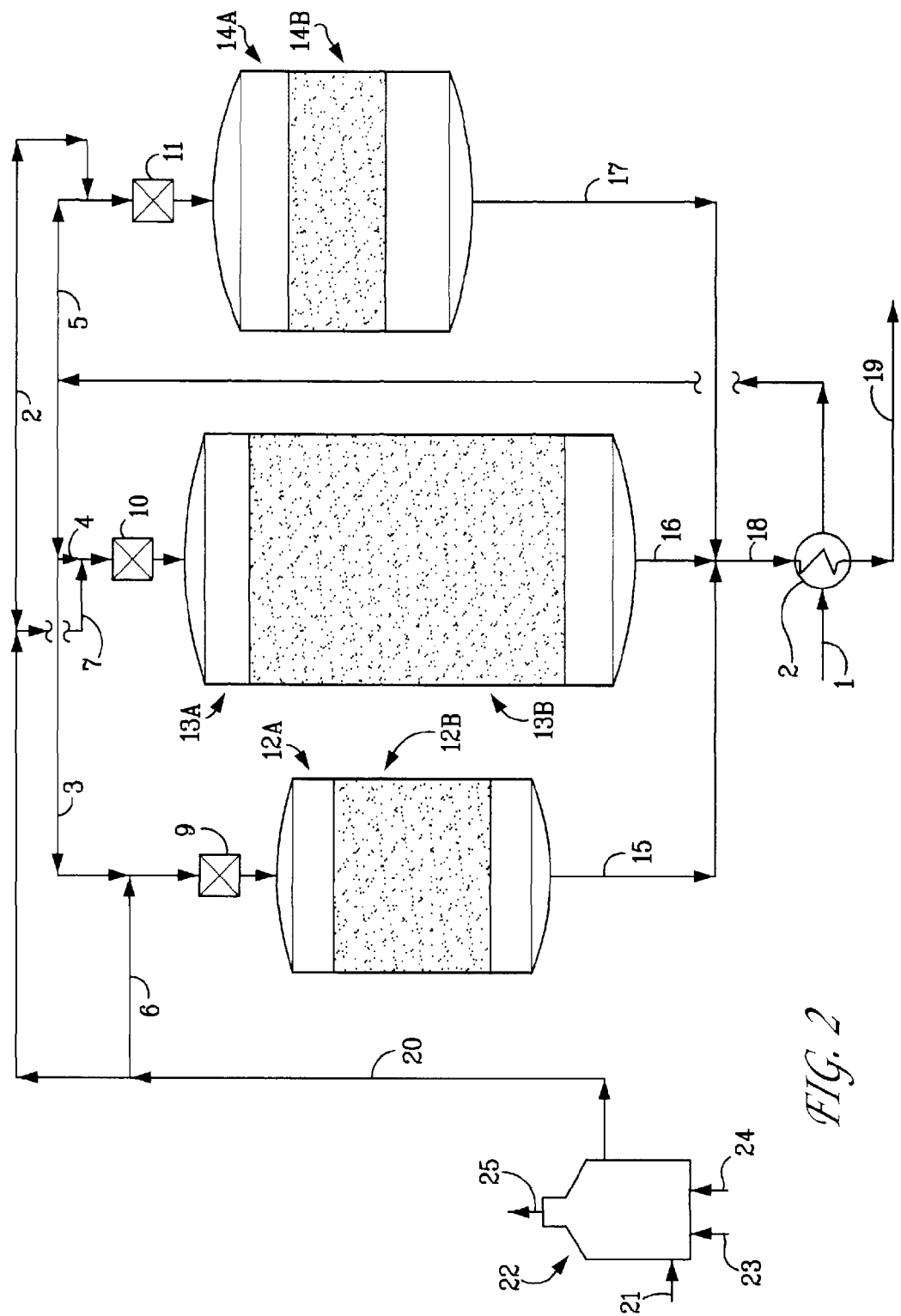
FIG. 2 depicts a second embodiment of the invention where three reactor vessels which are arranged in series to comprise the reactor train with each vessel in this embodiment having different length, diameter, volume, and/or catalyst quantity than the other vessels.

A second embodiment of the present invention is illustrated in FIG. 2. In this illustration, three reactor vessels are shown in parallel. The distinction between this variation and the variation shown in FIG. 1 is that, unlike the single reactor vessel with multiple catalyst stages and with each stage having different volume as shown in FIG. 1, there is one catalyst stage in each of the reactor vessels in the present variation. The reactor vessels are designed such that to utilize the available streams effectively and result in optimum distribution of alcohol into each reactor vessel. Similar to the previous variation, each vessel in this arrangement has a different internal diameter, length, and volume than the other reactor vessels. In addition, the quantity of catalyst in each vessel is different than the quantity in other reactor vessels.

As FIG. 2 illustrates, the fresh butanol stream 1 is vaporized and pre-heated in heat exchanger 2 prior to being divided into three streams 3, 4, and 5. Stream 3 is mixed with superheated inert gas stream 6 in inline mixer 9 and fed to the first reactor vessel 12A which contains the catalyst bed 12B. In similar fashion, stream 4 is mixed with superheated inert gas stream 7 in mixer 10 and fed to the second reactor vessel 13A which houses the catalyst bed 13B. Still in similar fashion, fresh butanol stream 5 is mixed with superheated inert gas stream 8 in inline mixer 11. The mixture is fed to reactor vessel 14A which holds the catalyst bed 14B. The exits streams 15 from reactor vessel 12, exit stream 16 from reactor vessel 13A, and exit stream 17 from reactor vessel 14A are combined and heat exchanged in exchanger 18 before taken to butylenes recovery and purification sections of the plant (not shown).

The operating conditions within the individual reactor vessels in this arrangement are such to achieve the desired performance criteria of optimum temperature profiles within the individual catalyst beds, complete conversion of butanol feedstock, and >99% selectivity to butylenes product. The ranges for these conditions include the following. Typically, the inlet temperature to each reactor vessel is between 250 to 520° C. and the outlet in the range of 220 to 480° C. The weight hourly space velocity (WHSV) of the butanol in each vessel is in the range of 0.001 to 10 kg butanol per hour per kg of catalyst. The weight ratio of the inert gas to butanol in the inlet to this stage is between 0.05 to 10 kg butanol to inert gas. Finally, the operating pressure within each reactor vessel may range from 1 to 50 barg.

To those skilled in the art, the design features as detailed in above paragraphs and the accompanying figures offer major technical advances and make it possible to realize numerous improvements and advantages over the previous arts. These advances and improvements are noted in the following paragraphs.

As explained before, the catalytic dehydration of butanol to butylenes is highly endothermic and requires considerable supply of energy to initiate the reaction and drive it to completion. The reaction produces one mole of water for each mole of butanol reacted according to:

$$C_4H_9OH \rightarrow C_4H_8 + H_2O$$

This reaction requires about 325 kcal per kg of butylenes at the normal operating temperatures of 350°-400° C.

Competing reactions may also take place producing the undesirable by-product such as ethers and other hydrocarbons.

The key is to minimize the formation of the by-products and maximize the selectivity to butylenes product by the optimum arrangement and size of the reactor stages and the staged addition of butanol and the heat supplying inert gas. A further consideration is to limit the secondary reaction of butylenes to other hydrocarbons which results in lower selectivity and yield.

The kinetics of the primary reaction are very sensitive to the operating temperature regime within the catalyst bed. At the inlet to the reactor, the temperature has to be high enough to initiate the reactions. If the temperature of the gas mixture is too high at the inlet region to the catalyst, degradation and side reactions of butanol will occur resulting in unwanted products. This reduces selectivity and yield to the desired butylenes product. As reactants pass through each catalyst bed, the temperature is continuously decreased toward the end of the catalyst bed due to the endothermicity of the reactions. At the outlet of the catalyst bed, if the temperature is allowed to cool significantly because of inadequate supply of sensible energy, either butanol conversion is not complete thus requiring recovery and recycle of unreacted butanol or secondary reactions can occur resulting in unwanted by-products such as aldehydes and ethers. Therefore, the temperature profile through the catalyst bed is very critical to optimum performance.

Three design features in this invention combine to result in optimum temperature profile within the individual reactors. First, the multiple staging of the reactors into variable volume compartments allows for the optimum distribution and residence time of the reactant alcohol and inert gas through each stage. The variable volume is achieved by varying the internal diameter of each reactor stage, varying the length of each stage, and/or varying the volume of the catalyst bed within each stage. Stages may have continuously variable internal diameter from the inlet of the stage to the outlet of the stage. The optimization of volume and thus the residence time distribution of the reactants is an important consideration in the kinetics of the dehydration reaction and therefore the optimum full and even utilization of the individual catalyst beds within the reactor stages.

Second, both the butanol feed and the heat supplying inert gas to each stage are separately and independently fed, controlled, and heated prior to being mixed and distributed to the individual reactor stages. This makes it possible to avoid super-heating of butanol and its thermal degradation and formation of coke precursor. In addition, this feature allows the optimum utilization of the heat carrying inert gas in relation to the amount of butanol feed rate. This optimization requires the balancing of sufficient energy supply to each stage but not excessive amounts which will result in economic disadvantage. The design also balances the formation of the water of reaction and the heat supplying inert gas. Furthermore, the design eliminates the formation of by-products such as ether, aldehydes, or other hydrocarbons.

The third design improvement embodied in this invention stems from the kinetics of the dehydration reaction and is based on arranging the catalyst stages and selecting the operating conditions in each stage in order to make it possible for the complete conversion of butanol through the individual reactor stages. Therefore, the costly butanol recovery and recycle are avoided in this processing scheme.

A further improvement of the present invention is that the economic life of each catalyst bed comprising the reactor train is considerably increased due to the optimum temperature profile within each stage. Therefore, frequent regenerations required in older technologies are avoided. The catalyst employed in this process may be high surface area aluminas, silica-alumina, zeolites, or other suitable catalysts as are described in the patent literature. See for example U.S. Pat. Nos. 4,260,845, 4,302,357, 4,529,827, 4,670,620, 4,873,392, and 6,489,515, and US patent application 2010/0249476. The longer catalyst life as realized from the present invention makes it possible for improved asset utilization and efficiency and allows for longer cycle time of the catalyst beds before unit shutdown and catalyst replacement are needed.

A further improvement resulting from the reactor design and the staged process for introducing butanol feed and the heat supplying inert gas into each stage and/or reactor vessel is that each stage may be by-passed to control the production rate or make it possible to perform maintenance in that stage without losing efficiency or shutting down the whole process. Furthermore, this allows for partial or total removal of the catalyst bed in a particular stage without having to shut down the whole process.

In addition to the above improvements, other improvements can be readily realized from this invention by those experts familiar with the selective dehydration of alcohols to olefins.

EXAMPLES

The following experimental examples serve to illustrate the unique features of the present invention and the resulting performance of the dehydration system. An experimental pilot reactor was constructed to allow the simulation of the operating conditions within each reactor stage and the performance testing of the reactor design as taught in this invention. The reactor consisted of a 1 inch OD, 0.870 inch ID, 3.5 feet long fix-bed down flow reactor. The reactor was heated in a three-zone furnace whereby the temperature of each zone could be controlled independently to achieve a desired temperature profile within the catalyst bed. The reactor tube was equipped with a centrally positioned 3/16" thermowell which housed five stationary thermocouples that were equally spaced within the thermowell at 0", 2", 4", 6", and 8" measured from the top of the catalyst bed.

The catalyst used in these experiments was a commercially available high purity and surface area gamma alumina. Approximately 40 CC of this catalyst was loaded into the reactor. An equal volume of inert alpha alumina spheres was mixed with the active catalyst as diluent yielding a total bed volume of ~80 CC. In addition, the same inert alumina spheres were used as pre- and post-heat zones of the reactor. The complete inertness of the spheres was demonstrated under all the operating conditions by testing the pilot reactor with only the alpha alumina packed inside the reactor tube.

The experimental setup was designed for continuous operation, sampling, and analysis of the products. The operating conditions were selected such that to simulate the ranges of the operating conditions within a two-stage design. Two sets of inlet/outlet operating temperatures were simulated and tested. The experimental conditions were as shown in Table 1.

TABLE 1

| Experimental Conditions | | |
| --- | --- | --- |
|  | Test 1 | Test 2 |
| Pressure, barg | 6.45 | 6.45 |
| Inlet Temperature, °C. | 466 | 416 |
| Outlet Temperature, °C. | 375 | 325 |
| Feed Butanol Conc., mole % | 1.26 | 1.26 |
| Feed Water Conc., mole % | 98.74 | 98.74 |
| Butanol WHSV, g/hr/g cat. | 0.1 | 0.1 |

The performance measures in these tests included the determination of butanol conversion, the selectivity to butylenes, and the extent of by-products formation. The by-products which were analyzed included methane, ethane, propane, propylene, methanol, ethanol, propanol, butanol, acetaldehyde, 1-butane, 2-butane, acetone, diethyl ether, n-pentane, 1-pentene, 1-hexene, and n-hexane. The test results are summarized in Table 2.

Butanol conversion was determined by

% Conversion=(butanol in-butanol out)×100/butanol in

Butylenes selectivity was determined by:

Selectivity=butylenes formed×100/total products formed

TABLE 2

| Performance Data | | |
| --- | --- | --- |
|  | Test 1 | Test 2 |
| Butanol Conversion, % | 100 | 100 |
| Butylenes Selectivity, % | 97 | 99 |
| By-products Conc., % | ND | ND |

ND: Not Detected

The butylenes products formed in the two tests were further analyzed for the different butylene isomers. The results are summarized in Table 3.

TABLE 3

| Breakdown of Butylene Isomers | | |
| --- | --- | --- |
|  | Test 1 | Test 2 |
| 1-Butene, % | 28 | 43 |
| cis-2-Butene, % | 45 | 30 |
| trans-2-Butene, % | 27 | 27 |

The invention claimed is:

1. An adiabatic reactor train configured for application to the catalytic
   (a) dehydration of butanol to butylenes process wherein:
   (b) the train is comprised of several adiabatic gas phase reactor vessels,
   (c) the reactor vessels are connected in series or parallel configuration,
   (d) each reactor vessel has a different internal diameter, length and volume than the other vessels,
   (e) each reactor vessel contains a quantity of fixed bed catalyst whose amount is different than the quantity in the other vessels, and
   (f) each vessel is substantially circular.

2. The adiabatic reactor train configuration of claim 1 wherein each stage has continually variable internal diameter from the inlet of the stage to the outlet.

3. The adiabatic reactor train configuration of claim 1 wherein: the number of reactor vessels is between 2 and 10 and preferably between 2 and 5, and each reactor vessel has an internal diameter of between 0.5 to 10 meters at the inlet to the vessel and an internal diameter of between 0.7 and 15 meters at the outlet of the vessel, and each stage has a length of between 0.3 to 16 meters.

4. The adiabatic reactor train configuration of claim 1 wherein at least one reactor vessel is comprised of several stages, the stages are stacked in a series or parallel configuration, each stage has a different internal diameter, length and volume than the other stages, each stage contains a quantity of fixed bed catalyst whose amount is different than the quantity in the other stages within the reactor vessel, and each stage is substantially circular.

5. An adiabatic reactor train configured for application to the catalytic (a) dehydration of butanol to butylenes process wherein: (b) the train is comprised of several adiabatic gas phase reactor vessels, (c) the reactor vessels are connected in series or parallel configuration, (d) each reactor vessel has a different internal diameter, length and volume than the other vessels, (e) each reactor vessel contains a quantity of fixed bed catalyst whose amount is different than the quantity in the other vessels, and (f) each vessel is substantially circular; and wherein at least one reactor vessel is comprised of several stages, the stages are stacked in a series or parallel configuration, each stage has a different internal diameter, length and volume than the other stages, each stage contains a quantity of fixed bed catalyst whose amount is different than the quantity in the other stages within the reactor vessel.

6. The adiabatic reactor train configuration of claim 5 wherein each stage has continually variable internal diameter from the inlet of the stage to the outlet.

* * * * *